United States Patent
Ogawa

(10) Patent No.: US 10,570,082 B2
(45) Date of Patent: Feb. 25, 2020

(54) ACRYLIC ACID PRODUCTION EQUIPMENT, METHOD FOR PRODUCING ACRYLIC ACID, AND METHOD FOR STOPPING PRODUCTION OF ACRYLIC ACID IN SAID METHOD FOR PRODUCING ACRYLIC ACID

(71) Applicant: Mitsubishi Chemical Corporation, Chiyoda-ku (JP)

(72) Inventor: Yasushi Ogawa, Mie (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 15/622,811

(22) Filed: Jun. 14, 2017

(65) Prior Publication Data
US 2017/0283357 A1 Oct. 5, 2017

Related U.S. Application Data

(63) Continuation of application No. PCT/JP2015/085396, filed on Dec. 17, 2015.

(30) Foreign Application Priority Data

Dec. 19, 2014 (JP) .................................. 2014-257894

(51) Int. Cl.
*C07C 51/16* (2006.01)
*C07C 51/25* (2006.01)
*B01J 19/24* (2006.01)

(52) U.S. Cl.
CPC ............ *C07C 51/16* (2013.01); *C07C 51/252* (2013.01); *B01J 19/24* (2013.01);
(Continued)

(58) Field of Classification Search
CPC ....................................................... C07C 51/16
(Continued)

(56) References Cited

U.S. PATENT DOCUMENTS 4,121,917 A 10/1978 Baker et al.
5,624,470 A * 4/1997 Tanca .......................... C10J 3/54
422/185

(Continued)

FOREIGN PATENT DOCUMENTS

CN 1299805 A 6/2001
CN 1509797 A 7/2004
(Continued)

OTHER PUBLICATIONS

Extended European Search Report dated Nov. 7, 2017 in Patent Application No. 15870065.8.
International Search Report dated Mar. 15, 2016 in PCT/JP2015/085396, filed on Dec. 17, 2015( with English Translation).
Written Opinion dated Mar. 15, 2016 in PCT/JP2015/085396, filed on Dec. 17, 2015.

(Continued)

*Primary Examiner* — Huy Tram Nguyen
(74) *Attorney, Agent, or Firm* — Oblon, McClelland, Maier & Neustadt, L.L.P.

(57) ABSTRACT

The present invention relates to an acrylic acid production equipment which includes a raw material gasification apparatus for converting liquefied propylene into a propylene gas; an oxidation reaction apparatus for converting the propylene gas into crude acrylic acid; and a purification apparatus for converting the crude acrylic acid into acrylic acid, wherein the raw material gasification apparatus includes a heating apparatus in the inside thereof and also includes a heating apparatus in the periphery including at least a bottom of the raw material gasification apparatus, by which not only energy can be effectively utilized, but also it is possible to achieve a stopping operation efficiently and within a short time.

8 Claims, 2 Drawing Sheets

(52) U.S. Cl.
CPC .............. *B01J 2219/00103* (2013.01); *B01J 2219/00132* (2013.01); *B01J 2219/24* (2013.01)

(58) Field of Classification Search
USPC ........................................... 422/187
See application file for complete search history.

(56) References Cited

U.S. PATENT DOCUMENTS

| | | | |
|---|---|---|---|
| 7,198,766 | B1 | 4/2007 | Okazaki et al. |
| 2001/0003733 | A1 | 6/2001 | Nishimura et al. |
| 2003/0187299 | A1 | 10/2003 | Machhammer et al. |
| 2006/0111575 | A1 | 5/2006 | DeCourcy et al. |
| 2007/0066845 | A1 | 3/2007 | Okazaki et al. |
| 2007/0106089 | A1 | 5/2007 | Benderly et al. |
| 2007/0227874 | A1* | 10/2007 | Wolf-Eberhard ........ C10G 1/10 202/84 |
| 2007/0271932 | A1 | 11/2007 | Dutt et al. |
| 2010/0083670 | A1 | 4/2010 | Dutt et al. |
| 2011/0105784 | A1 | 5/2011 | Benderly et al. |

FOREIGN PATENT DOCUMENTS

| | | |
|---|---|---|
| CN | 1781594 A | 6/2006 |
| EP | 1 097 916 A2 | 5/2001 |
| JP | 2001-131109 | 5/2001 |

OTHER PUBLICATIONS

P.R Pujado et al. "Newest acrylonitrile process," Hydrocarbon Processing, May 1977, pp. 4.

European Office Action dated Apr. 12, 2019 in European Patent Application No. 15870065.8, 5 pages.

The First Office Action dated Jul. 2, 2019 in Chinese Patent Application No. 201580068818.X filed Jun. 16, 2017 with computer generated English translation.

Office Action (Examination Report) dated Sep. 11, 2019 in Indian Patent Application No. 201717020552 filed Jun. 13, 2017 with English translation.

Search Report and Written Opinion dated Sep. 25, 2019 in Brazilian Patent Application No. BR112017013187-0 filed Dec. 17, 2015 with English translation (7 pages).

* cited by examiner

ACRYLIC ACID PRODUCTION EQUIPMENT, METHOD FOR PRODUCING ACRYLIC ACID, AND METHOD FOR STOPPING PRODUCTION OF ACRYLIC ACID IN SAID METHOD FOR PRODUCING ACRYLIC ACID

TECHNICAL FIELD

The present invention relates to a production equipment of a chemical product and a method for stopping operation of production of a chemical product using the production equipment of the chemical product, and in particular, the invention relates to a production equipment suited for production of acrylic acid and a method for stopping production of acrylic acid using the production apparatus.

BACKGROUND ART

Among compounds which are used as raw materials for synthesizing chemical products, those which are a gas at ordinary temperature and atmospheric pressure, a boiling point thereof being, however, not so low, and can be easily liquefied through pressurization or cooling, are generally handled as a so-called liquefied gas in a state of liquid in a storage container, a transportation container, or the like. In particular, in the case where the liquefied gas is a combustible liquefied gas having combustibility, in order to inhibit explosion or combustion, it is necessary to strictly control the liquefied gas such that the storage container, the transportation container, or the like does not become high in temperature; and that oxygen is not incorporated, or the combustible liquefied gas does not leak out to the outside.

In the case of producing a chemical product through a gas phase oxidation reaction using the combustible liquefied gas as a raw material, in general, the combustible liquefied gas is subjected to solution sending from the storage container or the like to an evaporation apparatus or the like; the combustible liquefied gas is vaporized in the evaporation apparatus or the like; and subsequently, the vaporized combustible liquefied gas is transferred into a reactor, etc. for achieving a gas phase oxidation reaction, to produce a chemical product.

In the conventional art, in the evaporation apparatus or the like, it is performed to vaporize the combustible liquefied gas with a liquid heat transfer medium and recover, as a cold heat, a latent heat to be consumed on the vaporization, and utilize the latent heat for a heat transfer medium for cooling.

For example, Non-Patent Literature 1 describes that liquefied propylene and liquefied ammonia that are raw materials for producing acrylonitrile are vaporized with a glycol aqueous solution, and the glycol aqueous solution after heat exchange is used as a medium for cooling of a refrigeration machine.

Patent Literature 1 discloses a method in which liquefied propylene which is a raw material for producing acrylic acid is vaporized with a liquid heat transfer medium of 0° C. to 50° C., and the liquid heat transfer medium having been cooled with a latent heat required for the vaporization is used for a heat transfer medium for cooling of a heat exchanger of an auxiliary cooler of an acrylic acid collection column or an acrylic acid separation column.

CITATION LIST

Patent Literature

Patent Literature 1: JP-A-2001-131109

Non-Patent Literature

Non-Patent Literature 1: *Hydrocarbon Processing*, May, 1977, pp. 169-172, "Newest acrylonitrile process"

SUMMARY OF INVENTION

Technical Problem

However, according to the conventional art, for example, in the invention of Patent Literature 1 or the technical contents of Non-Patent Literature 1, a producing operation of a chemical product which effectively utilizes the latent heat to be consumed in the vaporization of the combustible liquefied gas on the occasion of producing a chemical product using the combustible liquefied gas as the raw material is disclosed. However, there was neither described nor suggested the matter of efficiently performing a stopping operation of the producing operation of chemical product.

Especially, in the case where in order to change the raw material from a combustible liquefied gas A to a combustible liquefied gas B, the producing operation of the chemical product is stopped, and the combustible liquefied gas A within the evaporation apparatus is removed to the outside of the system, or in the case where some fault is generated within the evaporation apparatus or the like, the producing operation of the chemical product is stopped for the purpose of inspecting the inside, and the combustible liquefied gas within the evaporation apparatus is removed to the outside of the system, in particular, if the handling amount of the combustible liquefied gas is large, the production equipment of the chemical product of the conventional art was a very non-efficient equipment for performing the operation stopping operation, and it took a long time from the commencement to the completion.

The present invention has been made for the purpose of solving the above-described problems of the conventional art. Namely, an object of the present invention is to provide a production equipment of a chemical product wherein a chemical product is produced by using, as a raw material, at least one combustible liquefied gas selected from the group consisting of ammonia and a hydrocarbon having 3 carbon atoms or 4 carbon atoms, wherein not only a chemical product can be produced with effectively utilizing energy, but also it is possible to achieve a stopping operation efficiently and within a short time; and a method for stopping producing operation of a chemical product by the production equipment of the chemical product.

Solution to Problem

In order to achieve the above-described object, the inventor of the present invention made extensive and intensive investigations. As a result, it has been found that in a production equipment of the chemical product wherein a chemical product is produced by using a combustible liquefied gas as a raw material, when the production equipment of the chemical product includes a raw material gasification step of vaporizing the combustible liquefied gas, an oxidation reaction step of converting the vaporized raw material into a crude chemical product through an oxidation reaction, and a purification step of purifying the crude chemical product to form a chemical product, and an evaporation apparatus to be used in the raw material gasification step includes the following configuration.

Specifically, it has been found that when the production equipment of the chemical product in which the evaporation apparatus to be used in the raw material gasification step includes a heat transfer apparatus for vaporizing the combustible liquefied gas in the inside of the evaporation apparatus and also includes a heating apparatus for heating a part of the periphery including at least a bottom of the evaporation apparatus; a line for feeding a liquid heat transfer medium into the heat transfer apparatus is connected; and a line for subjecting the liquid heat transfer medium to solution sending from the heat transfer apparatus to a cooling medium feed system is connected is used for production of the above-described chemical product, in particular, even in the case where the handling amount of the combustible liquefied gas is large, or the case where a proportion of a surface area of the evaporation apparatus is small relative to a capacity thereof, not only the recovery of a latent heat of the combustible liquefied gas can be efficiently performed, but also a stopping operation of the producing operation for the chemical product can be completed safely and within in a short period of time.

Above all, it has been found that the production equipment of the chemical product according to the present invention is suitable as a equipment for producing acrylic acid from liquefied propylene.

The present invention has been achieved on a basis of such findings, and the gist thereof is as follows.

[1] A production equipment of the chemical product wherein a chemical product is produced, including a raw material gasification step of using, as a raw material, at least one combustible liquefied gas selected from the group consisting of ammonia and a hydrocarbon having three carbon atoms or four carbon atoms and vaporizing the combustible liquefied gas; an oxidation reaction step of converting the vaporized raw material into a crude chemical product through to an oxidation reaction; and a purification step of purifying the crude chemical product to form a chemical product, wherein an evaporation apparatus to be used in the raw material gasification step includes a heat transfer apparatus for vaporizing the combustible liquefied gas in the inside of the evaporation apparatus and also includes a heating apparatus for heating a part of the periphery including at least a bottom of the evaporation apparatus; and a line for feeding a liquid heat transfer medium into the heat transfer apparatus is connected, and a line for subjecting the liquid heat transfer medium to solution sending from the heat transfer apparatus to a cooling medium feed system is also connected.

[2] The production equipment of the chemical product as set forth in the above [1], wherein the heating apparatus is a steam tracing or an electric heater.

[3] The production equipment of the chemical product as set forth in the above [1] or [2], wherein the evaporation apparatus is covered by a heat insulator.

[4] The production equipment of the chemical product as set forth in any one of the above [1] to [3], wherein the combustible liquefied gas is at least one selected from the group consisting of ammonia, butane, 1-butene, isobutene, and propylene.

[5] The production equipment of the chemical product as set forth in any one of the above [1] to [4], wherein the chemical product is at least one selected from the group consisting of acrylonitrile, acrolein, methacrylic acid, acrylic acid, butene, and butadiene.

[6] A method for stopping producing operation of a chemical product using the production equipment of the chemical product as set forth in any one of the above [1] to [5], including stopping the reception of the combustible liquefied gas into the evaporation apparatus with operating the heat transfer apparatus, subsequently operating the heating apparatus, and further feeding an inert gas into the evaporation apparatus, to discharge the raw material gas within the evaporation apparatus to the outside of the evaporation apparatus.

[7] The method for stopping producing operation of a chemical product as set forth in the above [6], wherein a reception rate of the combustible liquefied gas into the evaporation apparatus in the producing operation of the chemical product is 1 ton or more per hour.

[8] An acrylic acid production equipment including a raw material gasification apparatus for converting liquefied propylene into a propylene gas, an oxidation reaction apparatus for converting the propylene gas into crude acrylic acid, and a purification apparatus for converting the crude acrylic acid into acrylic acid, wherein the raw material gasification apparatus includes a heat transfer apparatus in the inside thereof and also includes a heating apparatus in the periphery including at least a bottom of the raw material gasification apparatus.

[9] The acrylic acid production equipment as set forth in the above [8], wherein a line for feeding a heat transfer medium into the heat transfer apparatus is connected, and a line for subjecting the heat transfer medium to solution sending from the heat transfer apparatus to a cooling medium feed system is also connected.

[10] The acrylic acid production equipment as set forth in the above [8] or [9], wherein the heating apparatus is a steam tracing or an electric heater.

[11] The acrylic acid production equipment as set forth in any one of the above [8] to [10], wherein the raw material gasification apparatus is covered by a heat insulator.

[12] A method for producing acrylic acid using the acrylic acid production equipment as set forth in any one of the above [8] to [11], wherein the liquefied propylene is converted into a propylene gas by a raw material gasification apparatus; the propylene gas is converted into crude acrylic acid by an oxidation reaction apparatus; and the crude acrylic acid is converted into acrylic acid by a purification apparatus.

[13] The method for producing acrylic acid as set forth in the above [12], wherein a feed rate of the liquefied propylene into the raw material gasification apparatus is 1 ton or more per hour.

[14] A method for stopping producing acrylic acid in the method for producing acrylic acid as set forth in the above [12] or [13], including stopping the feed of liquefied propylene into the raw material gasification apparatus with operating the heat transfer apparatus, subsequently operating the heating apparatus, and further feeding an inert gas into the raw material gasification apparatus, to discharge propylene to the outside of the raw material gasification apparatus.

Effects of Invention

In accordance with the present invention, in a method of vaporizing a combustible liquefied gas by an evaporation apparatus and producing a chemical product through an oxidation reaction, a latent heat to be consumed by means of vaporization can be effectively recovered and utilized as cold heat, and furthermore, in stopping of the producing operation of the chemical product, it is possible to safely and rapidly remove the combustible liquefied gas remaining within the evaporation apparatus, so that it becomes possible to achieve the economical stopping operation.

In particular, in accordance with the acrylic acid production equipment according to the present invention, since the latent heat to be consumed by means of vaporization can be effectively recovered and utilized as a cold heat, the economical production of acrylic acid can be achieved.

DESCRIPTION OF EMBODIMENTS

A production equipment of the chemical product and a method for stopping producing operation of a chemical product using the production equipment of the chemical product according to the present invention are hereunder described in detail on a basis of the accompanying drawings.

Figure 1:
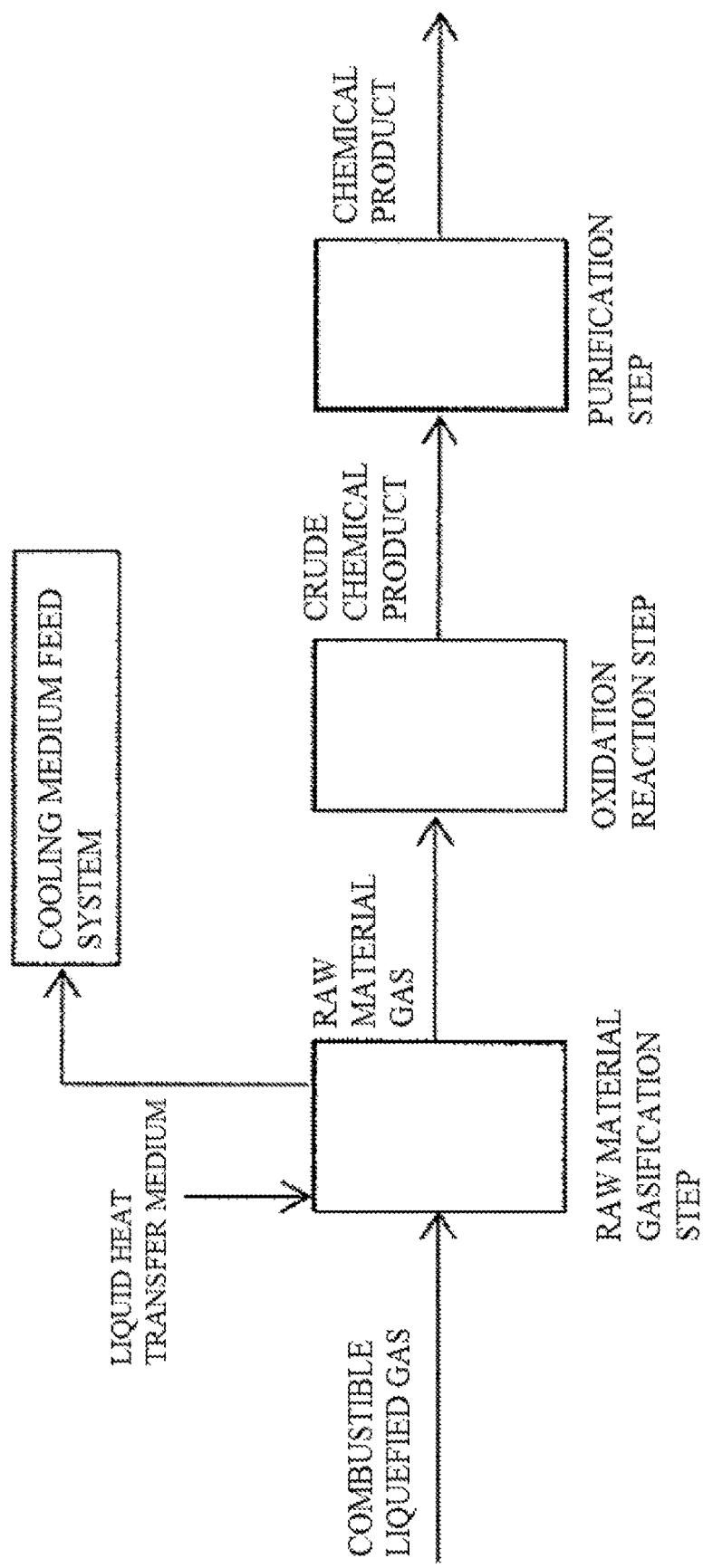
FIG. 1 is a conceptual scheme of a conventional production equipment of the chemical product.

FIG. 1 is concerned with a conventional production equipment of the chemical product and shows a production equipment of the chemical product wherein a chemical product is produced going through a raw material gasification step using a combustible liquefied gas as a raw material, an oxidation reaction step, and a purification step. In this production equipment of the chemical product, it is illustrated that while the combustible liquefied gas is vaporized with a liquid heat transfer medium in the raw material gasification step, a latent heat to be consumed in the vaporization is utilized as a cold heat.

The production apparatus of the chemical product according to the present invention includes a raw material gasification apparatus for vaporizing a combustible liquefied gas, an oxidation reaction apparatus for converting the vaporized combustible liquefied gas into a crude chemical product, and a purification apparatus for purifying the crude chemical product to form a chemical product, in which the raw material gasification apparatus includes a heat transfer apparatus in the inside thereof and also includes a heating apparatus in the periphery including at least a bottom of the raw material gasification apparatus.

Figure 2:
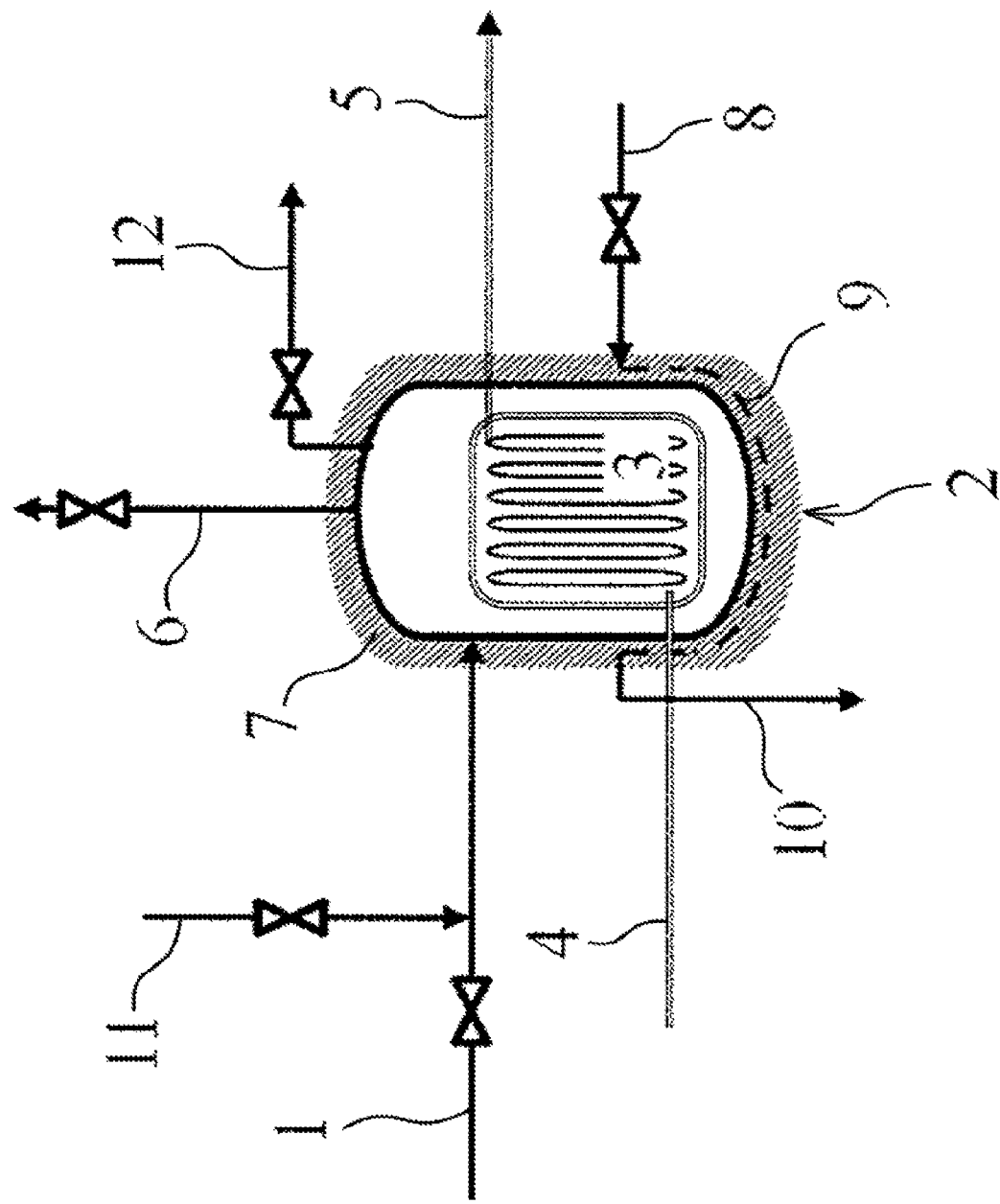
FIG. 2 is a figure showing an example of a raw material gasification apparatus in the present invention.

FIG. 2 is a figure showing an example of a raw material gasification apparatus for vaporizing a combustible liquefied gas in the production equipment of the chemical product according to the present invention.

The raw material gasification apparatus includes an evaporation apparatus (2) and is connected with a feed line (1) of combustible liquefied gas for feeding a combustible liquefied gas into the evaporation apparatus (2), an extraction line (6) of raw material gas for extracting the vaporized combustible liquefied gas, a feed line (11) of nitrogen for purge, and an extraction line (12) of exhaust gas for extracting an exhaust gas.

The evaporation apparatus (raw material gasification apparatus) (2) includes a heat transfer apparatus (3) in the inside thereof and includes a heating apparatus (a steam piping (9) for heating in FIG. 2) in the periphery including at least a bottom thereof.

In the heat transfer apparatus (3), a feed line (4) of liquid heat transfer medium for feeding a heat transfer medium and an extraction line (5) of liquid heat transfer medium for subjecting the heat transfer medium having fed an evaporation latent heat to solution sending to a cooling medium feed system are connected.

It is preferred that the periphery of the evaporation apparatus (2) is covered by a heat insulator (7). By arranging the heat insulator (7), the evaporation latent heat can be efficiently fed by the liquefied heat transfer medium, and it becomes possible to achieve the vaporization of the combustible liquefied gas. Although the heat insulator is not particularly limited, examples thereof include a glass wool, a polyurethane foam, and the like.

In the present invention, the heating apparatus (steam piping (9) for heating) is one to be used at the time of stopping the operation. As the heating apparatus, from the standpoint of maintenance, a simple and easy steam tracing or electric heater is preferred, and a steam tracing is more preferred.

In this connection, in FIG. 2, although the steam piping (9) for heating covers the bottom of the evaporation apparatus (2), the heating apparatus in the present invention may be a heating apparatus for heating a part of the periphery including at least the bottom of the evaporation apparatus.

The oxidation reaction apparatus is not particularly limited so long as it is able to produce a crude chemical product from the vaporized combustible liquefied gas. Conventionally known oxidation reaction apparatuses can be used, and examples thereof include a multitubular reactor, a plate type reactor, and the like.

The purification apparatus is not particularly limited so long as it is able to purify the crude chemical product obtained in the oxidation reaction apparatus to obtain a chemical product. Conventionally known purification apparatuses can be used, and examples thereof include a distillation column, an extraction column, a crystallization apparatus, and the like.

Next, the method for producing a chemical product using the production equipment of the chemical product according to the present invention is described.

In the method for producing a chemical product according to the present invention, at least one combustible liquefied gas selected from the group consisting of ammonia and a hydrocarbon having three carbon atoms or four carbon atoms is used as a raw material; the combustible liquefied gas is vaporized by a raw material gasification apparatus; the vaporized raw material gas is converted into a crude chemical product by an oxidation reaction apparatus; and the crude chemical product is converted into a chemical product by a purification apparatus.

First of all, the combustible liquefied gas is vaporized by the raw material gasification apparatus (raw material gasification step).

As illustrated in FIG. 2, in the raw material gasification apparatus (evaporation apparatus (2)), the combustible liquefied gas serving as a raw material is fed into the evaporation apparatus (2) through the feed line (1) of combustible liquefied gas. From the viewpoint of pressure resistance at the time of operation, it is preferable that a shape of the evaporation apparatus (2) is a cylindrical type. The direction of installation of the evaporation apparatus (2) may be either longitudinal or transverse. The combustible liquefied gas having been subjected to solution sending to the evaporation apparatus (2) is vaporized by the heat transfer apparatus (3) existing within the evaporation apparatus (2), and the vaporized raw material gas is sent to the oxidation reaction apparatus through the extraction line (6) of raw material gas and subjected to the oxidation reaction step.

In this connection, in order to vaporize the combustible liquefied gas, the liquid heat transfer medium is fed into the heat transfer apparatus (3) through the feed line (4) of liquid heat transfer medium, and the liquid heat transfer medium having fed an evaporation latent heat is extracted from the heat transfer apparatus through the extraction line (5) of liquid heat transfer medium and subjected to solution sending to a cooling medium feed system (not illustrated).

Although water is general as the liquid heat transfer medium, in the case where after feeding an evaporation latent heat, the temperature becomes 0° C. or lower, in order to avoid freezing from occurring, the liquid heat transfer medium may be an inorganic or organic aqueous solution, such as an ethylene glycol aqueous solution, an ammonium sulfate aqueous solution, etc. In order to efficiently perform heat exchange with the combustible liquefied gas, it is preferred to make a heat transfer area of the heat transfer apparatus (3) large. Examples of the heat transfer apparatus include a plate type, a multitubular type, and the like.

In the present invention, it is preferred that a feed rate of liquefied propylene into the evaporation apparatus (2) is 1 ton or more per hour. When the feed rate is 1 ton or more per hour, a proportion of a heat loss to be caused due to heat radiation into air becomes sufficiently small, and hence, such is preferred. The feed rate is more preferably 2 tons or more, and still more preferably 4 tons or more per hour. An upper limit of the feed rate is preferably 20 tons or less, and more preferably 15 tons or less per hour from various viewpoints, for example, when the equipment is made excessively large in size, the production costs becomes extremely high, and a load at the time of maintenance increases, so that it becomes difficult to take measures to meet the situation at the time when a disaster is happened, such as an earthquake or fire, etc. in case.

In the present invention, a heating temperature within the evaporation apparatus (2) is preferably from −20 to 20° C., more preferably from −15 to 15° C., and still more preferably from −10 to 10° C. By regulating the heating temperature to −20 to 20° C., a cold heat of a temperature which is hardly obtained by means of simple cooling with the open air or river water can be recovered with a less loss.

In the present invention, an operation pressure within the evaporation apparatus (2) is preferably from 200 to 1,000 kPa, more preferably from 250 to 800 kPa, and still more preferably from 300 to 600 kPa. By regulating the operation pressure to 200 to 1,000 kPa, the pressure that is necessary and sufficient for feeding the raw material gas into the oxidation reaction step can be obtained.

The raw material gas which has been vaporized and sent to the oxidation reaction apparatus forms a crude chemical product in this oxidation reaction apparatus (oxidation reaction step).

As for conditions of the oxidation reaction step, in mixing with an air-containing gas for oxidation, a gas composition to be formed is avoided from an explosive composition. In addition, as for the formation of an unintended explosive composition, for example, it is exemplified to take a measure of emergency shutdown of the plant, or the like.

The thus obtained crude chemical product is purified by the purification apparatus to obtain a chemical product (purification step).

As for conditions of the purification step, for the purpose of avoiding clogging or damage of the device following the polymerization, there are exemplified a lowering of the operation temperature due to pressure reduction, addition of a polymerization inhibitor, dissipation of the retention part, and the like.

In the present invention, on the occasion of stopping the production of the chemical product, the feed of the raw material gas (combustible liquefied gas) is stopped with operating the heat transfer apparatus of the raw material gasification apparatus; subsequently, the heating apparatus is operated; and furthermore, the inert gas is fed into the raw material gasification apparatus, to discharge the raw material gas to the outside of the raw material gasification apparatus.

Subsequently, the operation stopping method is described.

As illustrated in FIG. 2, an operation of closing a valve of the feed line (1) of combustible liquid gas with continuing the operation of the heat transfer apparatus (3), an operation of closing a valve of the extraction line (6) of raw material gas, and an operation of opening a valve of the extraction line (12) of exhaust gas are performed. According to these operations, the removal of the combustible liquefied gas remaining within the evaporation apparatus (2) to the outside of the evaporation apparatus (2) is commenced.

In this connection, by continuing the operation of the heat transfer apparatus (3), although the amount of the combustible liquefied gas remaining within the evaporation apparatus (2) is reduced, a reduction rate of the combustible liquefied gas becomes lower. The residual amount of the combustible liquefied gas within the evaporation apparatus (2) or the internal pressure can be measured by a liquid level indicator, a pressure gauge, or the like installed in the evaporation apparatus (2), and according to a decrease of the liquid amount and a reduction of the pressure, the valve of the feed line (8) of steam is gradually opened, to commence heating of the evaporation apparatus (2). Furthermore, after confirming the matter that the pressure has been sufficiently reduced, by opening a valve of the feed line (11) of nitrogen for purge, the combustible liquefied gas remaining within the feed line (1) of combustible liquefied gas and the evaporation apparatus (2) can be purged with a nitrogen gas.

By performing the foregoing operation stopping method, it becomes possible to perform the stopping operation efficiently and within a short time.

In the operation stopping method, it is also preferred that the periphery of the evaporation apparatus (2) is covered by the heat insulator (7). Due to the existence of the heat insulator (7), it becomes possible to efficiently perform heating by the steam piping (9) for heating, and it becomes possible to perform the stopping operation within a short time.

The method for stopping producing operation of a chemical product according to the present invention is a method of stopping producing operation of the chemical product. As the handling amount of the combustible liquefied gas increases, in other words, as the capacity of the evaporation apparatus is larger, and the amount of heat required for the evaporation of the liquefied gas is larger, the method is more effective. As a scale thereof, a reception rate of the combustible liquefied gas into the evaporation apparatus (2) at the time of producing operation of a chemical product is preferably 1 ton or more, more preferably 2 tons or more, and still more preferably 4 tons or more, per hour.

The combustible liquefied gas which is used for the production equipment of the chemical product according to the present invention is a compound having a boiling point of −50° C. to ordinary temperature, a temperature of which is liquefiable even without including a very-low-temperature equipment, and is at least one combustible liquefied gas selected from the group consisting of ammonia and a hydrocarbon having three carbon atoms or four carbon atoms. Above all, in view of a general-purpose chemical product raw material, it is preferable that the combustible liquefied gas is at least one selected from the group consisting of ammonia, butane, 1-butene, isobutene, and propylene, and propylene is more preferable.

In view of the facts that the producing amount is large, and the large-sized producing equipment is used, the chemical product which is produced by the production equipment of the chemical product according to the present invention is preferably at least one selected from the group consisting of acrylonitrile, acrolein, methacrylic acid, acrylic acid, butene, and butadiene, and acrylic acid is more preferable.

EXAMPLES

Although the present invention is hereunder described in more detail by reference to the Examples, it should be construed that the present invention is by no means limited by the following Examples.

Example 1

Liquefied propylene was used as a raw material and converted into a propylene gas by the raw material gasification apparatus as in FIG. 2, and this was used and subjected to the gas phase oxidation reaction step, to obtain a crude acrylic acid-containing gas. Subsequently, the crude acrylic acid-containing gas was sent to the purification step, to obtain acrylic acid. The operation pressure of the evaporation apparatus was 500 kPa; water was used as the liquid heat transfer medium; the feed temperature was 7.4 to 8° C.; and the extraction temperature was 3.5 to 4° C. The extracted liquid heat transfer medium was subjected to solution sending to the cooling medium feed system. The operation was performed in such a state for a half year and then stopped.

The feed of propylene into the oxidation reaction step and the feed of liquefied propylene into the evaporation apparatus were stopped, and the extraction line of exhaust gas was opened. The feed of water which is the liquid heat transfer medium was continued so as to keep the pressure of the evaporation apparatus at 500 kPa. As a result, a reduction of the pressure was confirmed after elapsing approximately 30 minutes, and therefore, the feed line of steam of the steam piping for heating was gradually opened, and the system was regulated such that the pressure was 500 kPa. After a while, the pressure was reduced regardless of the feed amount of the steam, and subsequently, after elapsing 2 hours, a pressure difference from the open air was reduced to 10 kPa. Therefore, the feed of nitrogen from the feed line of combustible liquefied gas was commenced with continuing the feed of a small amount of steam. It took 3 hours until the propylene was not detected by a gas detector installed in the extraction line of exhaust gas. For the sake of safety, the purge with a nitrogen gas was further continued for one hour, and the discharge of residual propylene was then finished. The time required for the discharge was 6.5 hours in total.

Comparative Example 1

The operation for stopping operation was performed in the same manner as in Example 1, except that the discharge of residual propylene was performed without performing the feed of steam into the evaporation apparatus. As a result, it took approximately 8 hours until the pressure difference from the open air of the evaporation apparatus became less than 10 kPa. Subsequently, the purge with nitrogen was performed in a flow rate of 1.5 times that in Example 1. However, it took approximately a half day until the propylene was not detected by the gas detector. For the sake of safety, the purge with nitrogen was further continued for 4 hours and then finished. The time required for the discharge was approximately one day.

While the present invention has been described in detail and with reference to specific embodiments thereof, it will be apparent to one skilled in the art that various changes and modifications can be made therein without departing from the spirit and scope thereof. The present application is based on a Japanese patent application filed on Dec. 19, 2014 (Japanese Patent Application No. 2014-257894), and the contents are incorporated herein by reference.

REFERENCE SIGNS LIST

1: Feed line of combustible liquefied gas
2: Evaporation apparatus
3: Heat transfer apparatus
4: Feed line of liquid heat transfer medium
5: Extraction line of liquid heat transfer medium
6: Extraction line of raw material gas
7: Heat insulator
8: Feed line of steam
9: Seam piping for heating
10: Extraction line of condensed water
11: Feed line of nitrogen for purge
12: Extraction line for exhaust gas

The invention claimed is:

1. An acrylic acid production equipment, comprising:
a raw material gasification apparatus for converting liquefied propylene into a propylene gas,
an oxidation reaction apparatus for converting the propylene gas into crude acrylic acid, and
a purification apparatus for converting the crude acrylic acid into acrylic acid,
wherein
the raw material gasification apparatus comprises:
a heat transfer apparatus inside, and
a heating apparatus in a periphery including at least a bottom of the raw material gasification apparatus,
a liquid raw material feed line connected to the gasification apparatus,
an extraction line for gasified raw material connecting the raw material gasification apparatus and the oxidation reaction apparatus, and
an extraction line for exhaust gas;
wherein a heat transfer medium of the heat transfer apparatus inside and a heating medium of the heating apparatus in a periphery are different.

2. The acrylic acid production equipment according to claim 1, further comprising:
a line for feeding a heat transfer medium into the heat transfer apparatus, and
a line for subjecting the heat transfer medium to solution sending from the heat transfer apparatus to a cooling medium feed system.

3. The acrylic acid production equipment according to claim 1, wherein the heating apparatus comprises steam tracing or an electric heater.

4. The acrylic acid production equipment according to claim 1, wherein the raw material gasification apparatus is covered by a heat insulator.

5. A method for producing acrylic acid with the acrylic acid production equipment according to claim 1, the method comprising:

converting liquefied propylene into a propylene gas by the raw material gasification apparatus;

converting the propylene gas into crude acrylic acid by the oxidation reaction apparatus; and converting the crude acrylic acid into acrylic acid by the purification apparatus.

6. The method according to claim 5, wherein a feed rate of the liquefied propylene into the raw material gasification apparatus is 1 ton or more per hour.

7. A method for stopping producing acrylic acid in the method according to claim 5, the method comprising stopping a feed of the liquefied propylene into the raw material gasification apparatus while operating the heat transfer apparatus, subsequently operating the heating apparatus, and further feeding an inert gas into the raw material gasification apparatus, to discharge propylene to an outside of the raw material gasification apparatus.

8. The acrylic acid production equipment according to claim 1, further comprising an inert gas purge line connected to the liquid raw material feed line.

* * * * *